United States Patent
Groot et al.

(10) Patent No.: US 12,004,460 B2
(45) Date of Patent: Jun. 11, 2024

(54) DOWNY MILDEW RESISTANT IMPATIENS

(71) Applicant: SYNGENTA PARTICIPATIONS AG, Basel (CH)

(72) Inventors: Antonius Jacobus Gerardus Groot, Andijk (NL); Nevena Folkerts-Radmanovic, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/958,887

(22) PCT Filed: Feb. 6, 2019

(86) PCT No.: PCT/US2019/016787
§ 371 (c)(1),
(2) Date: Jun. 29, 2020

(87) PCT Pub. No.: WO2019/157017
PCT Pub. Date: Aug. 15, 2019

(65) Prior Publication Data
US 2021/0235646 A1    Aug. 5, 2021

Related U.S. Application Data

(60) Provisional application No. 62/628,441, filed on Feb. 9, 2018.

(51) Int. Cl.
*A01H 6/16* (2018.01)
*A01H 1/00* (2006.01)
*A01H 5/02* (2018.01)

(52) U.S. Cl.
CPC ........... *A01H 6/165* (2018.05); *A01H 1/1255* (2021.01); *A01H 5/02* (2013.01)

(58) Field of Classification Search
CPC .............................. A01H 6/165; A01H 1/1255
See application file for complete search history.

(56) References Cited

U.S. PATENT DOCUMENTS

2018/0271045 A1* 9/2018 Warfield ................ A01H 6/165
2019/0059311 A1   2/2019 Kerley et al.

OTHER PUBLICATIONS

Daughtrey et al Plant Health Progress vol. 21 No. 3 pp. 214-216 (Year: 2020).*
Salgado-Salazar et al., Polymorphic SSR Markers for *Plasmopara obducens* (Peronosporaceae), the Newly Emergent Downy Mildew Pathogen of *Impatiens* (Balsaminaceae), Applications in Plant Sciences, Nov. 10, 2015, 3, (11): 1500073.
International Search Report for International Application No. PCT/US19/16787 dated Apr. 10, 2019.
Hansen et al., Virginia Cooperative Education, Virginia Tech, Virginia State University, May 21, 2013 [Retreived on Mar. 21, 2019] . Retrieved from the Internet: techworks.lib.vt.edu/handle/10919/48289>.
Lane et al., First Report of Impatiens downy mildew (*Plasmopara obducens*) in the UK, Plant Pathology, 2005, 54, 2, 243.

* cited by examiner

*Primary Examiner* — David H Kruse
(74) *Attorney, Agent, or Firm* — Dale Skalla

(57) ABSTRACT

Up until now, all varieties of *Impatiens walleriana* are susceptible to *impatiens* downy mildew cause by the water mold, *Plasmopara obducens*. The present invention relates to novel *Impatiens walleriana* seed containing a genetic resistance to *Plasmopara obducens*. The present invention also relates to methods for creating novel *Impatiens walleriana* seed containing a genetic resistance to *Plasmopara obducens* and *Impatiens walleriana* seed produced by the method.

4 Claims, No Drawings

DOWNY MILDEW RESISTANT IMPATIENS

CROSS-REFERENCE TO RELATED APPLICATIONS

This application is a 371 of International Application No. PCT/US2019/016787, filed Feb. 6, 2019, which claims priority under 35 U.S.C. § 119 to U.S. Provisional Application No. 62/628,441, filed Feb. 9, 2018, which are incorporated herein in their entirety by reference.

BACKGROUND

*Impatiens* downy mildew is a disease affecting *Impatiens walleriana* cause by the water mold, *Plasmopara obducens*. The disease results in yellowing of the leaves followed by the appearance of white spores on the underside of the leaves. These white spores called sporangia spread the disease if they splash onto the leaves of another *impatiens* plant. The disease can also be spread by a longer lived resting form called oospores which are produced in the stems of infected plants. Fungicides can be used to protect plants from *impatiens* downy mildew, but infected plants cannot be cured. Up until now, all varieties of *Impatiens walleriana* are susceptible to *impatiens* downy mildew, and sales of *Impatiens walleriana* as garden plants have been sharply reduced since the wide spread emergence of *Impatiens* Downy Mildew.

SUMMARY OF THE INVENTION

In some embodiments, the invention provides an *Impatiens walleriana* seed containing a genetic resistance to *Plasmopara obducens*, wherein said seed has a pedigree which includes the plant AB1664-1.

In some embodiments, the invention provides the *Impatiens walleriana* plant grown from the seed of claim 1, wherein said seed contains genetic resistance to *Plasmopara obducens*.

In some embodiments, the invention provides the *Impatiens walleriana* plant of claim 2, wherein said seed contains genetic resistance to *Plasmopara obducens*, survives the growing season while susceptible plants succumb when grown under the same conditions.

In some embodiments, the invention provides the *Impatiens walleriana* plant of claim 2, wherein said seed contains genetic resistance to *Plasmopara obducens*, lives five, six, seven, eight, nine or ten weeks longer than susceptible plants when grown under the same conditions.

In some embodiments, the invention provides a method for producing F1 hybrid *Impatiens walleriana* seed comprising crossing a first parent *Impatiens* plant containing a genetic resistance to *Plasmopara obducens*, wherein said seed has a pedigree which includes the plant AB1664-1, with a second parent *Impatiens walleriana* plant and harvesting the resultant F1 hybrid *Impatiens walleriana* plant containing a genetic resistance to *Plasmopara obducens*.

In some embodiments, the invention provides an *Impatiens walleriana* seed containing a genetic resistance to *Plasmopara obducens*, wherein genetic resistance to *Plasmopara obducens* is obtainable from the plant AB1664-1.

In some embodiments, the invention provides an *Impatiens walleriana* seed containing a genetic resistance to *Plasmopara obducens*, wherein genetic resistance to *Plasmopara obducens* is obtained from the plant AB1664-1.

DETAILED DESCRIPTION OF THE INVENTION

The present invention provides an *Impatiens* plant containing a novel genetic resistance to *Plasmopara obducens*, wherein a sample of representative seed of said plant is deposited under NCIMB Accession No. 42721.

Wherein the *Impatiens* plant is an *Impatiens walleriana* plant.

Wherein the resistance allows the plant to survive the growing season.

In one embodiment, the *Impatiens* plant of the invention is *Impatiens walleriana*. The *Impatiens* plant may also belong to another species including, but not limited to *Impatiens hawkeri*, *Impatiens ecornuta*, *Impatiens grandulifera*, *Impatiens hongkongensis*, *Impatiens namchabarwensis*, *Impatiens noli-tangere*, *Impatiens parviflora*, and *Impatiens pallida*.

In one embodiment, the *Impatiens* plant according to the present invention is an annual plant.

There is also provided an *Impatiens* plant containing a genetic resistance to *Plasmopara obducens*, obtainable by crossing a first *Impatiens* plant containing an intermediate genetic resistance to *Plasmopara obducens* with a second *Impatiens* plant, wherein said first *Impatiens* plant is deposited under NCIMB Accession No. 42721.

There is also provided a seed containing a genetic resistance to *Plasmopara obducens*, wherein said seed is obtainable from a plant grown from seed deposited under NCIMB Accession No. 42721 or progeny thereof.

There is also provided an *Impatiens* seed containing a genetic resistance to *Plasmopara obducens*, wherein said seed has a pedigree which includes the plant AB1664-1, and wherein representative seed of said plant AB1664-1 has been deposited under NCIMB Accession No. 42721.

There is also provided an *Impatiens* seed containing a genetic resistance to *Plasmopara obducens*, wherein said genetic resistance is present in AB1664-1, a representative sample of seed which is deposited at NCIMB under Accession No. NCIMB 42721, or in a progeny or ancestor thereof comprising said genetic resistance to *Plasmopara obducens*.

Not to be limited by theory, in some embodiments, the genetic resistance to *Plasmopara obducens* present in AB1664-1 is encoded by one, two, three or more resistance genes.

In one embodiment, the genetic resistance to *Plasmopara obducens* is not in the natural genetic background of the resistant *Impatiens* plant. In one embodiment, the plant of the invention is an agronomically elite or cultivated *Impatiens* plant comprising a genetic resistance to *Plasmopara obducens*.

In one embodiment an *Impatiens* plant is provided that is resistant to *Plasmopara obducens*, to statistically the same extent as AB1664-1, a representative sample of seed which is deposited at NCIMB under Accession No. NCIMB 42721, when assessed using the same assay, particularly an assay as described in Example 3 below, and under identical environmental conditions, particularly under the same *Plasmopara obducens* pressure.

In one embodiment, the *Impatiens* plant of the invention is a hybrid. In one embodiment, the *Impatiens* plant of the invention is an inbred line.

There is also provided a tissue culture of cells produced from an *Impatiens* plant of the present invention, wherein said cells of the tissue culture are produced from a plant part selected from the group consisting of seed, leaf, pollen, embryo, cotyledon, hypocotyl, meristematic cell, root, root tip, pistil, anther, flower, stem, and petiole.

There is also provided an *Impatiens* plant regenerated from the tissue culture as herein described.

There is also provided pollen and/or an ovule of the plant of the present invention. In some embodiment, the invention provides a seed of the *Impatiens* plant AB1664-1, representative seed of said plant having been deposited under Accession No. NCIMB 42721.

In some embodiments, the invention provides an *Impatiens* plant AB1664-1 grown from the seed of *Impatiens* plant AB1664-1 representative seed of said plant having been deposited under Accession No. NCIMB 42721.

There is also provided a method for producing F1 hybrid *Impatiens* seed comprising crossing a first parent *Impatiens* plant with a second parent *Impatiens* plant and harvesting the resultant F1 hybrid *Impatiens* seed, wherein said first or second parent *Impatiens* plant is the *Impatiens* plant of the present invention. In further embodiments, the invention provides an *Impatiens* plant produced by this method.

The present invention further relates to a method of producing the disclosed *Impatiens* plant and seed by crossing a *Plasmopara obducens* resistant plant of the instant invention with another *Impatiens* plant. The invention also relates to the transfer of the genetic *Plasmopara obducens* resistance into genera other than *Impatiens*.

In order to transfer the heritable genetic resistance to another plant, backcross breeding can be used. For this a desirable homozygous cultivar or inbred is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent (*Plasmopara obducens* resistance) are selected and repeatedly crossed (backcrossed) to the recurrent parent. The resulting plant is expected to have the attributes of the recurrent parent (e.g., cultivar) and the desirable trait transferred from the donor parent. Descriptions of other breeding methods that are commonly used for different traits and crops can be found in one of several reference books (Allard, 1960; Simmonds, 1979; Fehr, 1987).

Disease Monitoring and Assessment

Downy Mildew Resistance can be identified by monitoring the crop regularly for disease development as indicated by sporulation initially. Assessments are made (as deemed appropriate at time of assessment) of sporulation, crop vigor, DMR, leaf discoloration and flower count.

The following assessment scales were used:

Sporulation (0-5 Scale)
  0 No sporulation
  1 1 or two small lesions (<5% leaf area affected)
  2 Large area of one leaf affected or several leaves partly affected (5-10% leaf area affected)
  3 Several leaves affected (10-25% leaf area affected)
  4 Most leaves partly affected (25-75% leaf area affected)
  5 Little or no leaf area with no sporulation (>75% leaf area affected)

Leaf Discoloration (0-5 Scale)—See FIG. 3
  0 No visible discoloration of leaves
  1 Slight discoloration (one or 2 leaves showing small area of discoloration)
  2 Slight-moderate discoloration
  3 Moderate discoloration (half of leaf area discolored)
  4 Moderate-severe discoloration
  5 Severe discoloration of all foliage DMR (0-5 Scale)—see FIG. 4
  0 No plant remaining to assess
  1 Plant is dying, heavy leaf drop
  2 Plant is clearly unhealthy, severe leaf drop, stem elongations and sporulation under leaves
  3 Noticeable leaf drop, sporulation under the leaves, clear stem elongations
  4 Sporulation present under the leaves, some stem elongations
  5 No sporulation visible, no leaf drop, plant looks healthy High resistance plant varieties that highly restrict the growth and/or development of the specified pest and/or the damage it causes under normal pest pressure when compared to susceptible varieties. These plant varieties may, however, exhibit some symptoms or damage under heavy pest pressure. In some embodiments, the invention provides a high resistance plant.

Intermediate resistant plant varieties that highly restrict the growth and/or development of the specified pest and/or the damage it causes, but may exhibit a greater range of symptoms or damage compared to high resistant varieties. Intermediate resistant plant varieties will still show less severe symptoms or damage than susceptible plant varieties when grown similar environmental conditions and/or pest pressure. In some embodiments, the invention provides a medium resistance plant.

In some embodiments, the invention provides a resistant plant which survives the growing season under pest pressure.

A suitable donor parent for the genetic resistance to *Plasmopara obducens* according to the present invention may be the *Impatiens* plant AB1664-1, representative seeds of which have been deposited at NCIMB (Ferguson Building, Craibstone Estate, Bucksburn, Aberdeen AB219YA, Scotland) under NCIMB 42721 on Jan. 27, 2017.

Accordingly, the person skilled in the art, based on the description of the present invention and in possession of *Impatiens* plant AB1664-1, representative seed of which is deposited under accession Number NCIMB 42721, has no difficulty transferring the genetic resistance to *Plasmopara obducens* according to the present invention to any other *Impatiens* plant using any breeding technique well known in the art.

There is also provided hybrid seed produced by the method of the present invention.

There is also provided a hybrid plant or its parts produced by growing hybrid seed of the present invention. There is also provided seed containing a broad spectrum genetic resistance to *Plasmopara obducens* produced from the hybrid plant of the present invention.

There is also provided viable *Impatiens* seeds deposited under NCIMB Accession No. 42721 and plants grown from said deposited seeds and the progeny thereof, wherein the progeny contain the genetic determinate for resistance to *Plasmopara obducens*.

DEFINITIONS

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants.

As used herein, the term "breeding", and grammatical variants thereof, refer to any process that generates a progeny individual. Breeding can be sexual or asexual, or any combination thereof. Exemplary non-limiting types of breeding include crossing, selfing, doubled haploid derivative generation, polyploidization and combinations thereof. The phenotype of the flower of the present invention can be readily and stably transferred by breeding to progeny.

As used herein, the term "hybrid" in the context of plant breeding refers to a plant that is the offspring of genetically dissimilar parents produced by crossing plants of different lines or breeds or species, including but not limited to the cross between two inbred lines.

A "cultivated *Impatiens* plant" or an "elite *Impatiens* plant" is understood within the scope of the invention to refer to a plant that is no longer in the natural state but has been developed by human care and for human use and/or consumption. "Cultivated plants" are further understood to exclude those wild-type species which comprise the trait being subject of this invention as a natural trait and/or part of their natural genetics.

A "plant" is any plant at any stage of development.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, callus, and the like.

As used herein, the term "population" means a genetically heterogeneous collection of plants sharing a common genetic derivation. A population of plants typically corresponds to 10 or more plants which have more or less the same phenotype at maturity in terms of flower color appearance.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the F1, the F2, or any subsequent generation.

"Resistance to *Plasmopara obducens*" or "resistant plant" refers to the plant's capability to resist attack or infestation by *Plasmopara obducens*. *Impatiens* plant is resistant to at least *Plasmopara obducens*, and to significantly the same level of resistance, as that of *Impatiens* plant AB1664-1, representative seed of which is deposited under accession Number NCIMB 42721.

"Trait" is understood within the scope of the invention to refer to a characteristic or phenotype. A trait may be inherited in a dominant or recessive manner, or may be monogenic or polygenic.

"Dominant" is understood within the scope of the invention to refer to an allele which determines the phenotype when present in the heterozygous or homozygous state.

A "recessive" allele is only displayed when present in the homozygous state.

Seed Deposit

Seed of the variety AB1664-1 (an *Impatiens* plant) has been deposited under the terms of the Budapest Treaty on Jan. 27, 2017 at the NCIMB, Craibstone, Aberdeen, UK under number NCIMB 42721.

The seed deposit was made in the name of Syngenta Participations AG, Basel 4002, Switzerland.

EXAMPLES

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

Example 1

Resistance Breeding

Commercial Syngenta *Impatiens walleriana* varieties were tested for downy mildew resistance in an outdoor trial in 2008 in the Netherlands. Plants were allowed to become infected by spores present in the environment. Of 255 varieties tested, 21 varieties with less symptoms of infection were saved to be crossed. Seed from these crosses were first grown in an indoor trial and then the most promising plants were tested in a further outdoor trial. One plant, AB1664-1, survived the season in the outdoor trial and was chosen to be the source of resistance for breeding into commercial *Impatiens walleriana*.

Example 2

Creation of Downy Mildew Resistant Commercial Lines

Genetic resistance from line AB1664-1 in the form of a genetic determinate *Plasmopara obducens* resistance was crossed into elite germplasm to create *Impatiens* IDMR Red, *Impatiens* IDMR Orange, *Impatiens* IDMR Purple, *Impatiens* IDMR White, *Impatiens* IDMR Carmine, *Impatiens* IDMR Bicolour Rose Pink, and *Impatiens* IDMR Orange Star.

Example 3

Experimental Design for Evaluation of Novel Cultivars for Tolerance to Downy Mildew Infection Caused by *Plasmopara obducens*

Glasshouse Phase

Plants established well in the glasshouse environment but, despite manipulation of the environment and introduction of additional sporulating infector plants, symptoms of downy mildew were not observed in the test plants as quickly as anticipated.

Sporulation caused by downy mildew was first observed on 26 Jun. 2017 in susceptible cultivar Xtreme White, 3 weeks after the introduction of infector plants to the trial area. An assessment of sporulation on all plots was carried out immediately and then on a weekly basis until the plants were ready to plant out in the field 2 weeks later. At all three of these assessment timings there were significant differences in incidence of sporulation (% of plants affected) and level of sporulation (0-5 scale) visible between the susceptible cultivar Xtreme White and the IDMR cultivars. See Table 1 for a summary of these results and FIG. 5 for incidence of sporulation at the last glasshouse assessment.

In the field phase of the trial, the trial randomization was maintained, with 30 plants per plot planted at 30 cm spacings in a 5×6 arrangement in the field, as shown in FIG. 2.

Inoculation

Plants of the susceptible cultivar Xtreme White were used as infector plants. A downy mildew spore suspension was prepared by washing spores from heavily infected *Impatiens* material. The spore suspension was sprayed onto the supplied plants which were then covered and kept humid for 24 hours to allow infection to occur. After 10 days plants were again covered to encourage sporulation of any downy mildew present and thus to confirm that infection had occurred. The inoculation process was successful and sufficient infector plants were available with which to introduce infection to the trial. Infector plants were introduced into the trial area 6 days after the test plants were received and set up.

It was important not to introduce so much infector material that the test plants were overwhelmed by infection and, as such, only 4 infector plants were initially introduced to the trial. After 12 days, when no sporulation was evident in Xtreme White, additional infector plants were introduced, along with damped-up capillary matting to maintain a humid environment conducive to downy mildew infection and sporulation.

TABLE 1

Severity and incidence of downy mildew infection in glasshouse phase of trial

| | | Assessment Date | | | | |
|---|---|---|---|---|---|---|
| | | Jun. 26, 2017 | | Jul. 3, 2017 | | Jul. 10, 2017 | |
| Trt. No. | Cultivar Name | Sporulation (0-5) | Incidence (%) | Sporulation (0-5) | Incidence (%) | Sporulation (0-5) | Incidence (%) |
| 1 | Xtreme White | 1.38 a | 68.99 a | 2.10 a | 95.55 a | 4.58 a | 100.00 a |
| 2 | IDMR Red | 0.02 b | 1.12 cd | 0.04 b | 2.06 b | 0.88 cd | 54.17 cd |
| 3 | IDMR Orange | 0.06 b | 4.05 cd | 0.00 b | 0.00 b | 0.54 d | 43.75 de |
| 4 | IDMR Purple | 0.00 b | 0.00 d | 0.04 b | 2.06 b | 0.67 d | 35.42 e |
| 5 | IDMR White | 0.13 b | 8.06 be | 0.06 b | 2.58 b | 1.31 b | 62.50 be |
| 6 | IDMR Carmine | 0.21 b | 17.72 b | 0.02 b | 0.75 b | 1.17 be | 70.83 b |
| 7 | TDMR Bicolour Rose Pink | 0.04 b | 2.88 cd | 0.02 b | 0.75 b | 0.92 bed | 52.08 cd |
| 8 | TDMR Orange Star | 0.02 b | 1.12 cd | 0.00 b | 0.00 b | 0.81 cd | 54.17 cd |
| LSD P = 0.05 | | 0.340 | 2.001 | 0.209 | 0.803 | 0.425 | 12.518 |
| Standard Deviation | | 0.231 | 1.361 | 0.142 | 0.546 | 0.289 | 8.511 |
| CV | | 99.83 | 47.84 | 49.53 | 124.41 | 21.25 | 14.4 |
| Replicate F | | 0.620 | 0.65 < J | 0.934 | 1.461 | 0.919 | 1.388 |
| Replicate Prob(F) | | 0.609 | 0.5863 | 0.441t | 0.2537 | 0.4488 | 0.2740 |
| Treatment F | | 16.291 | 13.337 | 107.27 < J | 3.08 < J | 84.296 | 21.428 |
| Treatment Prob(F) | | 0.0001 | 0.0001 | 0.0001 | 0.021 I | 0.0001 | 0.0001 |

Means followed by the same letter do not significantly differ (P = 0.05, LSD)

It is interesting to note that at the second assessment timing, incidence of sporulation has actually decreased in some cultivars. It is likely that infected foliage had fallen from plants and, due to the natural cycle of downy mildew infection, further sporulation had not yet occurred on retained foliage.

Susceptible cultivar Xtreme White developed severe downy mildew infection rapidly once sporulation was first observed. At all three assessment dates Xtreme White had significantly higher levels of infection and a higher proportion of plants affected than any IDMR cultivars.

There were also differences in infection level between IDMR cultivars, with IDMR Purple generally having a low severity and incidence of infection and IDMR Carmine and IDMR White showing the highest levels of infection across the 3 assessments.

During this phase of the trial it was noted that, whilst sporulation levels were lower in the IDMR cultivars than in Xtreme White, there was some discoloration of the foliage (as shown in FIG. 3 in Materials and Methods) in the IDMR cultivars that was not present in Xtreme White. It seemed that this was perhaps a sign of infection being present in the plant, but that sporulation and leaf drop were somehow being prevented. An assessment was made of this leaf discoloration (on a 0-5 scale as described in Materials and Methods) at the final glasshouse assessment and then again during field phase assessments. At the request of the sponsor, an assessment of DMR was introduced at the final assessment and continued through the field assessments. The DMR score took into account a number of different plant effects caused by downy mildew infection, as shown in Materials and Methods. The results of the leaf discoloration (higher scores indicate more discoloration) and DMR assessments (lower scores indicate more severe downy mildew effects) are shown in Table 2

TABLE 2

DMR and leaf discoloration assessment in glasshouse phase

|  |  | Assessment Date | |
|---|---|---|---|
| Trt. No. | Cultivar Name | Jul. 10, 2017 DMR (0-5) | Jul. 10, 2017 Discoloration (0-5) |
| 1 | Xtreme White | 2.85 c | 0.07 e |
| 2 | IDMR Red | 4.13 a | 1.10 d |
| 3 | IDMR Oran e | 3.96 ab | 1.27 cd |
| 4 | IDMR Purple | 4.13 a | 1.36 cd |
| 5 | IDMR White | 3.67 b | 2.09 b |
| 6 | IDMR Carmine | 4.00 a | 0.96 d |
| 7 | IDMR Bicolour Rose Pink | 3.81 ab | 1.64 be |
| 8 | IDMR Orange Star | 3.90 ab | 2.81 a |
| LSD P = 0.05 |  | 0.328 | 1.12 |
| Standard Deviation |  | 0.223 | 0.76f |
| CV |  | 5.86 | 11.85 |
| Replicate F |  | 0.61J1 | 1.379 |
| Replicate Prob(F) |  | 0.6157 | 0.276f |
| Treatment F |  | 13.785 | 38.456 |
| Treatment Prob(F) |  | 0.0001 | 0.0001 |

Means followed by the same letter do not significantly differ (P = 0.05, LSD)

Xtreme White scored significantly lower for leaf discoloration whereas all 7 IDMR cultivars showed a moderate level of discoloration. There were some significant differences between IDMR cultivars, with IDMR Orange Star and IDMR White displaying the highest levels of discoloration. No correlation could be found between levels of sporulation and levels of discoloration in the 7 IDMR cultivars, so whilst the discoloration is likely to be related to tolerance to downy mildew, we were not able to show a direct link between downy mildew sporulation and discoloration.

Xtreme White scored significantly lower on the DMR scale than all the test cultivars, indicating more severe effects from downy mildew. IDMR White scored the lowest DMR score of all the IDMR cultivars, corresponding with the sporulation assessments discussed above. IDMR Purple was again scored as the best of the test varieties at this stage. IDMR Carmine actually ranks better for DMR score than it does for the sporulation severity and incidence. This suggests that, although sporulation was present at higher levels, this cultivar was not showing as many of the other visual symptoms assessed when scoring DMR, e.g. stem elongation and leaf drop.

Field Phase

In mid-July, once plants achieved a marketable size, the trial was planted out in a field site. At this stage all of the Xtreme White plants and approximately half of the IDMR cultivar plants had downy mildew sporulation present Whilst plants established as well as could be expected, the effects of downy mildew infection caused rapid deterioration of plants of Xtreme White. Assessments were carried out one week after planting and then on three further occasions, ending in mid-September.

At the first post planting assessment, assessments were made of sporulation, DMR and leaf discoloration. Sporulation incidence was found to be 100 in all plots and whilst all 7 IDMR cultivars had significantly lower levels of sporulation than Xtreme White, there were only slight significant differences between the cultivars. IDMR Orange had statistically significantly lower levels of sporulation than IDMR Purple, although this difference was small. There were no significant differences between any other IDMR cultivar combinations (see FIG. 6). Other statistical differences were seen between cultivars with regards to sporulation at this time and, given the practicalities of assessing in a field situation, sporulation severity was not assessed again. Instead, DMR and flower count were used as a measure of the effect of downy mildew infection. A summary of all DMR data and flower counts from the field phase of the study is shown in Table 3.

TABLE 3

Summary of assessment data from field phase of trial

| Trt. No. | Cultivar name | Assessment Date | | | | | |
|---|---|---|---|---|---|---|---|
|  |  | Jul. 19, 2017 DMR (0-5) | Aug. 1, 2017 DMR (0-5) | Aug. 16, 2017 DMR (0-5) | Sep. 13, 2017 DMR (0-5) | Aug. 16, 2017 Flower Count | Sep. 13, 2017 Flower Count |
| 1 | Xtreme White | 1.00 d | 0.00 d | 0.00 e | 0.00 f |  |  |
| 2 | IDMR Red | 3.04 a | 2.38 a | 1.43 a | 1.56 ab | 3.83 be | 1.18 e |
| 3 | IDMR Orange | 2.96 ab | 2.24 ab | 1.31 ab | 1.48 be | 4.93 b | 1.40 be |
| 4 | IDMR Purple | 2.77 e | 2.15 ab | 1.49 a | 1.67 a | 4.00 be | 4.35 a |
| 5 | IDMR White | 2.98 ab | 1.50 e | 1.10 b | 1.15 e | 1.50 d | 0.19 de |
| 6 | IDMR Carmine | 2.96 ab | 2.00 b | 1.31 ab | 1.35 ed | 2.52 ed | 1.01 e |
| 7 | IDMR Bicolour Rose Pink | 3.08 a | 2.02 b | 1.23 ab | 1.40 bed | 2.79 ed | 2.73 ab |
| 8 | IDMR Orange Star | 2.85 be | 2.44 a | 1.49 a | 1.27 de | 7.85 a | 0.72 ed |
| LSD P = 0.05 |  | 0.171 | 0.341 | 0.061 | 0.176 | 1.549 | 2.825 |
| Standard Deviation |  | 0.116 | 0.232 | 0.041t | 0.120 | 1.042 | 1.921 |
| CV |  | 4.3 | 12.6 | 12.79t | 9.7 | 26.6 | 32.22 |
| Replicate F |  | 12.722 | 4.078 | 1.928 | 1.473 | 0.927 | 0.307 |
| Replicate Prob(F) |  | 0.0001 | 0.0198 | 0.156 | 0.2507 | 0.4481 | 0.8197 |
| Treatment F |  | 143.356 | 47.236 | 41.406 | 76.79S | 15.705 | 15.326 |
| Treatment Prob(F) |  | 0.0001 | 0.0001 | 0.0001 | 0.0001 | 0.0001 | 0.0001 |

Means followed by the same letter do not significantly differ (P = 0.05, LSD)

The susceptible cultivar Xtreme White did not persist for long in the field, being severely affected by downy mildew to such an extent that no leaf material remained for assessment after just 3 weeks in the field and all plants scored 0 for DMR. All 7 IDMR cultivars scored significantly better for DMR than Xtreme White at all assessments in the field, although downy mildew was present on all plants. Whilst the IDRM cultivars performed much better than Xtreme White, the DMR scores they achieved are still indicative of clearly unhealthy plants. All cultivars exhibited stem elongation, leaf drop and low levels of flowering. FIG. 7 shows all 8 trial cultivars one week after planting out. The IDMR cultivars are beginning to show signs of infection other than sporulation at this stage, whilst Xtreme White shows severe infection effect.

The progression of DMR scores over time during the field phase of the trial is shown in FIG. 8. It is interesting to note a slight increase in the DMR score at the final assessment for a number of the IDMR cultivars. A certain amount of regeneration of foliage sometimes occurs in downy mildew-infected *Impatiens* plants following loss of infected leaves, and this regeneration is reflected in these increased DMR scores.

Alongside assessments of DMR, discoloration of foliage was also assessed in the field phase of the trial. Xtreme White showed no discoloration at the first of three assessments and for the remaining assessments had no foliage to assess. There were significant differences between the level of discoloration seen in the IDMR cultivars and these differences can be seen in Table 4.

TABLE 4

Discoloration of foliage in field phase of trial

| Trt No. | Cultivar Name | Jul. 18, 2017 Discoloration _(0-5) | Aug. 1, 2017 Discoloration (_0-5) | Aug. 16, 2017 Discoloration _(0-5 |
|---|---|---|---|---|
| 1 | Xtreme White | 0.00 f | | |
| 2 | IDMR Red | 2.06 d | 2.31 a | 2.17 cd |
| 3 | IDMR Orange | 2.85 b | 2.45 a | 2.14 cd |
| 4 | IDMR Purple | 3.08 b | 2.25 a | 2.58 ab |
| 5 | IDMR White | 1.57 e | 2.56 a | 1.88 d |
| 6 | IDMR Carmine | 1.75 de | 1.90 a | 2.15 cd |
| 7 | IDMR Bicolour Rose Pink | 2.48 c | 2.35 a | 2.31 be |
| 8 | IDMR Orange Star | 3.71 a | 2.38 a | 2.75 a |
| LSD P = 0.05 | | 0.324 | 0.440 | 0.410 |
| Standard Deviation | | 0.220 | 0.296 | 0.276 |
| CV | | 10.05 | 12.81 | 12.1 |
| Replicate F | | 1.729 | 2.844 | 0.668 |
| Replicate Prob(F) | | 0.1918 | 0.0668 | 0.5824 |
| Treatment F | | 106.413 | 2.004 | 4.608 |
| Treatment Prob(F) | | 0.0001 | 0.11 | 0.0053 |

Means followed by the same letter do not significantly differ (P = 0.05. LSD)

There are some small statistically significant differences in DMR scores between cultivars although the ranking of cultivars at the different assessment timings does vary. Flower counts were significantly different between the test cultivars although, again, the ranking of varieties based on this score varies with assessment date. The main differences between IDMR cultivars are summarized below.

What is claimed:

1. An *Impatiens walleriana* seed of variety AB1664-1 for which representative seed was deposited as NCIMB Accession No. 42721.

2. An *Impatiens walleriana* plant grown from the seed of claim 1.

3. A method for producing F1 hybrid *Impatiens walleriana* seed comprising crossing a first parent *Impatiens* plant with a second parent *Impatiens walleriana* plant and harvesting the resultant F1 hybrid *Impatiens walleriana* plant, and wherein the first or second parent is the plant of claim 2.

4. An F1 *Impatiens walleriana* plant produced by growing the seed of claim 3.

* * * * *